(12) United States Patent
Blaney et al.

(10) Patent No.: US 6,506,790 B1
(45) Date of Patent: Jan. 14, 2003

(54) COMPOUNDS AND METHODS

(75) Inventors: Frank E. Blaney, Harlow (GB);
William E Bondinell, Wayne, PA (US);
James A. Chan, West Chester, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/914,502

(22) PCT Filed: Mar. 10, 2000

(86) PCT No.: PCT/US00/06210

§ 371 (c)(1),
(2), (4) Date: Mar. 10, 1999

(87) PCT Pub. No.: WO00/53175

PCT Pub. Date: Sep. 14, 2000

Related U.S. Application Data

(60) Provisional application No. 60/123,607, filed on Mar. 10, 1999.

(51) Int. Cl.$^7$ .................................................. A01N 43/02
(52) U.S. Cl. ........................ 514/449; 514/451; 514/453; 514/454; 514/455; 549/385
(58) Field of Search .................................. 514/449, 451, 514/453, 454, 455, 394, 385

(56) References Cited

U.S. PATENT DOCUMENTS

| | | |
|---|---|---|
| 5,962,462 A | 10/1999 | Mills et al. |
| 6,013,644 A | 1/2000 | Mills et al. |

*Primary Examiner*—Dwayne C. Jones
*Assistant Examiner*—C. Delacroix-Muirheid
(74) *Attorney, Agent, or Firm*—Nora Stein-Fernandez; Stephen A. Venetianer; Charles M. Kinzig

(57) ABSTRACT

This invention relates to substituted benzo[1,2-b:5,4-b'] dipyran-4-amines which are modulators, agonists or antagonists, of the CCR5 receptor. In addition, this invention relates to the treatment and prevention of disease states mediated by CCR5, including, but not limited to, asthma and a topic disorders (for example, a topic dermatitis and allergies), rheumatoid arthritis, sarcoidosis and other fibrotic diseases, atherosclerosis, psoriasis, autoimmune diseases such as multiple sclerosis, and inflammatory bowel disease, all in mammals, by the use of substituted benzo[1,2-b:5,4-b']dipyran-4-amines which are CCR5 receptor antagonists. Furthermore, since CD8+T cells have been implicated in COPD, CCR5 may play a role in their recruitment and therefore antagonists to CCR5 could provide potential therpeutic in the treatment of COPD. Also, since CCR5 is a co-receptor for the entry of HIV into cells, selective receptor modulators may be useful in the treatment of HIV infection.

10 Claims, No Drawings

COMPOUNDS AND METHODS

This is a 371 of International Application PCT/US00/06210, filed Mar. 10, 2000, which claims benefit from Provisional Application No. 60/123,607, filed Mar. 10, 1999.

FIELD OF THE INVENTION

This invention relates to substituted benzo[1,2-b:5,4-b'] dipyran4-amines which are modulators, agonists or antagonists, of the CC chemokine receptor CC-CKR5 now designated as CCR5 (Nature Medicine, 2: 1174–8, 1996). In addition, this invention relates to the treatment and prevention of disease states mediated by CCR5.

BACKGROUND OF THE INVENTION

T cells are not only key regulators of the immune response to infectious agents but are believed critical for the initiation and maintenance of the inflammatory reaction in a variety of chronic diseases. Increased numbers or enhanced activation state of T cells, especially CD4+ T cells, have been demonstrated in the synovium of individuals with rheumatoid arthritis (M. J. Elliott and R. N. Maini, Int. Arch. Allergy Immunol. 104: 112–1125, 1994), in the bronchial mucosa of asthmatics (C. J. Corrigan and A. B. Kay, Immunol. Today 13: 501–506, 1992), in the lesions of multiple sclerosis (R. Martin and H. F. McFarland, Crit. Rev. Clin. Lab. Sci. 32: 121–182, 1995), in psoriatic lesions (J. L. Jones, J. Berth-Jone, A. Fletcher and P. E. Hutchinson, J. Pathol. 174: 77–82, 1994) and in the fatty streaks of atherosclerosis (R. Ross, Annu. Rev. Physiol. 57: 791–804, 1995).

T cells, as well as other inflammatory cells, will migrate into tissues in response to the production of a variety chemotactic factors. Among these factors are a superfamily of 8–12 kDa proteins known as the chemokines. These proteins share structural features such as the presence of 3–4 conserved cysteine residues. RANTES, which stands for Regulated upon Activation Normal T cell Expressed and Secreted, is a 8 kDa protein member of CC branch of the chemokine family. These proteins recruit and activate immune and inflammatory cells through an interaction with G-protein coupled receptors. The CC branch is defined by the absence of an intervening amino acid residue between the first two cysteine residues and members of this family predominately elicit the migration of mononuclear cells, eosinophils and basophils (M. Baggiolini, B. Dewald, and B. Moser, Adv. Immunol. 55: 97–179, 1994; and J. J. Oppenheim, C. O. C. Zachariae, N. Mukaida, and K. Matsushima, Annu. Rev. Immunol. 9: 617–648, 1991).

RANTES potently produces chemotaxis of T cells, basophils, eosinophils, monocytes and mast cells. RANTES was originally identified as gene product induced late after antigen activation of T-cells (T. J. Schall, J. Jongstra, B. J. Dyer, J. Jorgensen, et al., J. Immunol. 141:1018–1025, 1988), however, RANTES has been shown to be synthesized and secreted by a diverse group of cells that include epithelial and endothelial cells (C. Stellato, L. A. Beck, G. A. Gorgone, D. Proud, et al., J. Immunol. 155: 410–418, 1995; and A. Marfaing-Koka, O. Devergne, G. Gorgone, A. Portier, et al., J. Immunol. 154: 1870–1878, 1994), synovial fibroblasts (P. Rathanaswami, M. Hachicha, M. Sadick, T. J. Schall, et al., J. Biol. Chem. 268: 5834–5839, 1993) and dermal fibroblasts (M. Sticherling, M. Kupper, F. Koltrowitz, E. Bornscheuer, et al., J. Invest. Dermatol. 105: 585–591, 1995), mesangial cells (G. Wolf, S. Aberle, F. Thaiss, et al., Kidney Int. 44: 795–804, 1994) and platelets (Y. Koameyoshi, A. Dorschner, A. I. Mallet, E. Christophers, et al., J. Exp. Med. 176: 587–592, 1992). In these cells RANTES mRNA is rapidly upregulated in response to IL-1 or TNFα. Although RANTES mRNA is not usually detected in normal tissues (J. M. Pattison, P. J. Nelson, and A. M. Krensky, Clin. Immunother. 4: 1–8, 1995), increased mRNA or protein has been found in diseases characterized by a mononuclear infiltrate. For example, RANTES mRNA was visualized using in situ hybridization in renal allografts undergoing rejection (J. M. Pattison, P. J. Nelson, and A. M. Krensky, Clin. Immunother. 4: 1–8, 1995; and K. C. Nadeau, H. Azuma and N. I. Tilney, Proc. Natl. Acad. USA 92: 8729–8733, 1995) in the skin of a topic dermatitis patients after exposure to antigen (S. Ying, L. Taborda-Barata, Q. Meng, M. Humbert, et al., J. Exp. Med. 181: 2153–2159, 1995), and in endothelial cells of coronary arteries undergoing accelerated atherosclerosis after cardiac transplant (J. M. Pattison, P. J. Nelson, and A. M. Krensky, Clin. Immunother. 4: 1–8, 1995). Further, increased immunoreactive protein for RANTES has been detected in bronchoalveolar lavage fluid (R. Alam, J. York, M. Boyers, et al.,Am. J. Resp. Crit. Care Med. 149: A951, 1994) and sputum from asthmatic individuals (C. M. Gelder, P. S. Thomas, D. H. Yates, I. M. Adcock, et al., Thorax 50: 1033–1037, 1995).

Several receptors have been identified that bind RANTES. In particular, CCR5, when expressed in either HEK 293 cells or CHO cells, binds RANTES. This receptor is expressed in T-cells and in monocytes and macrophages, immune/inflammatory cells which are important in the maintenance of a chronic inflammatory reaction. Pharmacological characterization of CCR5 indicates sirnilarities to the RANTES binding site observed on isolated T cells. Therefore, antagonism of RANTES' action on CCR5, as well as antagonism of other natural modulators of CCR5, should inhibit the recruitment of T cells into inflammatory lesions and provide a novel therapeutic approach for the treatment of a topic and autoimmune disorders.

Since T cells express CCR5, selective receptor modulators of CCR5, particularly antagonists, are likely to provide beneficial effects in diseases including, but not limited to, asthma and a topic disorders (for example, a topic dermatitis and allergies), rheumatoid arthritis, atherosclerosis, psoriasis, sarcoidosis and other fibrotic diseases, autoimmune diseases such as multiple sclerosis, and inflammatory bowel disease, all in mammals, preferably humans. Furtermore since CD8+ T cells have been implicated in COPD, CCR5 may play a role in their recruitment and therefore antagonists to CCR5 could provide potential therpeutic in the treatment of COPD. Also since CCR5 is a co-receptor for the entry of HIV into cells, selective receptor modulators may be useful in the treatment of HIV infection.

Surprisingly, it has now been discovered that a class of non-peptide compounds, in particular substituted benzo[1, 2-b:5,4-b']dipyran-4-amines of formula (I), function as CCR5 receptor modulators, and therefore, have utility in the treatment and prevention of disease states mediated by CCR5 receptor mechanisms.

SUMMARY OF THE INVENTION

In one aspect, the present invention is to a genus of novel compounds of formula (I), or pharmaceutically active salts thereof, said compounds which are also useful in treating the above-mentioned CCR5-mediated disease states:

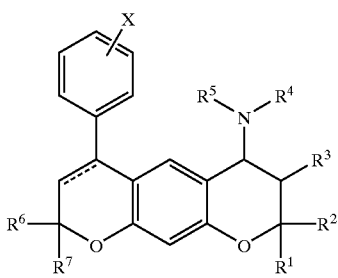

Formula (1)

wherein:

$R^1$, $R^2$, $R^6$, and $R^7$ are independently hydrogen or $C_{1-6}$alkyl;

$R^3$ is hydrogen or hydroxy;

$R^4$ is hydrogen or $C_{1-6}$alkyl;

$R^5$ is hydrogen, $C_{1-6}$alkyl, $C_{3-6}$cycloalkyl, or aralkyl; or, $NR^4R^5$ may form a heterocyclic ring having 5-, 6-, or 7-members, optionally containing one of oxygen, sulfur, or $NR^8$;

$R^8$ is hydrogen, $C_{1-6}$alkyl, or aralkyl;

X is hydrogen or one or more of $C_{1-6}$alkyl, $C_{2-6}$alkenyl, $C_{2-6}$alkynyl, $C_{3-6}$cycloalkyl, $C_{5-6}$cycloalkenyl, aralkyl, aryl, $CH_2NR^9R^{10}$, $CH_2OR^{11}$, $COR^{11}$, $CONR^9R^{10}$, $CO_2R^{11}$, cyano, trifluoromethyl, $NR^9R^{10}$, $NR^9COR^{11}$, $NR^9CONR^9R^{10}$ $NR^9CO_2R^{12}$, $NR^9SO_2R^{13}$, nitro, hydroxy, $C_{1-6}$alkoxy, $OC(O)R^{11}$, $OC(O)NR^9R^{10}$, $SR^{14}$, $SOR^{13}$, $SO_2R^{13}$, $SO_2NR^9R^{10}$ or halogen;

$R^9$ and $R^{10}$ are independently hydrogen, $C_{1-6}$alkyl, aralkyl or aryl; or $NR^9R^{10}$ forms a heterocyclic ring having 5-, 6-, or 7-members, optionally containing one oxygen, sulfur, or $NR^8$;

$R^{11}$ is hydrogen, $C_{1-6}$alkyl, aralkyl, aryl, or trifluoromethyl;

$R^{12}$ is $C_{1-6}$alkyl, aralkyl, aryl, or trifluoromethyl;

$R^{13}$ is $C_{1-6}$alkyl, aralkyl, aryl, or trifluoromethyl;

$R^{14}$ is hydrogen, $C_{1-6}$alkyl, aralkyl, aryl, or trifluoromethyl; and ==== is a single or a double bond.

In another aspect, the present invention is to a method of treating CCR5 mediated disease states, including, but not limited to, COPD, asthma and a topic disorders (for example, a topic dermatitis and allergies), rheumatoid arthritis, sarcoidosis and other fibrotic diseases, atherosclerosis, psoriasis, autoimmune diseases such as multiple sclerosis, inflammatory bowel disease, and HIV infection, all in mammals, preferably humans, comprising administering to such mammal in need thereof, a benzo[1,2-b:5,4-b']dipyran-4-amine of formula (I), or pharmaceutically active salts thereof.

In yet another aspect, the present invention is to pharmaceutical compositions comprising a compound of formula (I) and a pharmaceutically acceptable carrier therefor. In particular, the pharmaceutical compositions of the present invention are used for treating CCR5-mediated disease states, including, but not limited to,COPD asthma and a topic disorders (for example, a topic dermatitis and allergies), rheumatoid arthritis, sarcoidosis and other fibrotic diseases, atherosclerosis, psoriasis, autoimmune diseases such as multiple sclerosis, inflammatory bowel disease, and HIV infection.

DETAILED DESCRIPTION OF THE INVENTION

It has now been discovered that substituted benzo[1,2-b:5,4b']dipyran-4-amines of formula (I) are CCR5 receptor modulators. It has also now been discovered that selective inhibition of CCR5 receptor mechanisms by treatment with the receptor modulators of formula (I), or a pharmaceutically acceptable salt thereof, represents a novel therapeutic and preventative approach to the treatment of a variety of disease states, including, but not limited to, asthma and a topic disorders (for example, a topic dermatitis and allergies), rheumatoid arthritis, sarcoidosis and other fibrotic diseases, atherosclerosis, psoriasis, autoimmune diseases such as multiple sclerosis, and inflammatory bowel disease, all in mammals, preferably humans ("CCR5-mediated diseases"). Furthermore, since CD8+ cells have been implicated in COPD. CCR5 may play a role in their recruitment and therefore antagonists to CCR5 could provide potential therpeutic in their recruitment and COPD. Also, since CCR5 is a co-receptor for the entry of HIV into cells, selective receptor modulators may be useful in the treatment of HIV infection.

The term "alkyl" is used herein at all occurrences to mean a straight or branched chain radical of 1 to 6 carbon atoms, unless the chain length is limited thereto, including, but not limited to methyl, ethyl, n-propyl, isopropyl, n-butyl, sec-butyl, isobutyl, tert-butyl, and the like.

The terms "cycloalkyl" and "cyclic alkyl" are used herein at all occurrences to mean cyclic radicals, preferably comprising 3 to 6 carbon atoms which may be mono- or bicyclo-fused ring systems which may additionally include unsaturation, including, but not limited to, cyclopropyl, cyclopentyl, cyclohexyl, and the like.

The term "cycloalkenyl" is used herein to mean cyclic radicals, preferably of 5 to 6 carbons, which have at least one double bond between two of the carbon atoms in the ring, including but not limited to cyclopentenyl, cyclohexenyl, and the like.

The term "alkenyl" is used herein at all occurrences to mean a straight or branched chain radical of 2 to 6 carbon atoms, unless the length is limited thereto, wherein there is at least one double bond between two of the carbon atoms in the chain, including, but not limited to, ethenyl, 1-propenyl, 2-propenyl, 2-methyl-1-propenyl, 1-butenyl, 2-butenyl, and the like.

The term "alkynyl" is used herein at all occurrences to mean a straight or branched chain radical of 2 to 6 carbon atoms, unless the chain length is limited thereto, wherein there is at least one triple bond between two of the carbon atoms in the chain, including, but not limited to, acetylene, 1-propylene, 2-propylene, and the like.

The term "aryl" is used herein at all occurrences to mean 5–14-membered substituted or unsubstituted aromatic ring (s) or ring systems which may include bi- or tri-cyclic systems, including, but not limited to phenyl, naphthyl, and the like.

The term "aralkyl" is used herein at all occurrences to mean an aryl moiety as defined above, which is connected to a $C_1$ to $C_6$ alkyl moiety as defined above, for example, benzyl or phemethyl, and the like.

The term "alkoxy" is used herein at all occurrences to mean a straight or branched chain radical of 1 to 6 carbon atoms, unless the chain length is limited thereto, bonded to an oxygen atom, including, but not limited to, methoxy, ethoxy, n-propoxy, isopropoxy, and the like.

The terms "halo" or "halogen" are used interchangeably herein at all occurrences to mean radicals derived from the elements chlorine, fluorine, iodine and bromine.

The term "heterocyclic" is used herein at all occurrences to mean a saturated or partially unsaturated 5-, 6-, or 7-membered ring system (unless the cyclic ring system is otherwise limited) in which the ring optionally contains one other heteroatom selected from oxygen, sulfur, or $NR^8$, wherein $R^8$ is defined above, such as, but not limited to, piperazine or morpholine.

The term "CCR5 mediated disease state" is used herein at all occurrences to mean any disease state which is mediated (or modulated) by CCR5.

Suitably, pharmaceutically acceptable salts of formula (I) include, but are not limited to, salts with inorganic acids such as hydrochloride, sulfate, phosphate, diphosphate, hydrobromide, and nitrate, or salts with an organic acid such as malate, maleate, fumarate, tartrate, succinate, citrate, acetate, lactate, methanesulfonate, p-toluenesulfonate, palmitate, salicylate, and stearate.

The compounds of the invention can exist in unsolvated as well as solvated forms, including hydrated forms. In general, the solvated forms, with pharmaceutically acceptable solvents such as water, ethanol, and the like, are equivalent to the unsolvated forms for purposes of this invention.

The compounds of the present invention may contain one or more asymmetric carbon atoms and may exist in racemic and optically active forms. The stereocenters may be of any combination of R and S configuration, for example, (R,R), (R,S), (S,S) or (S,R). All of these compounds are within the scope of the present invention.

For the compounds of formula (I) various embodiments are as follows.

X is suitably hydrogen or one or more of $C_{1-6}$alkyl, $C_{2-6}$alkenyl, $C_{2-6}$alkynyl, $C_{3-6}$cycloalkyl, $C_{5-6}$cycloalkenyl, aralkyl, aryl, $CH_2NR^9R^{10}$, $CH_2OR^{11}$, $COR^{11}$, $CONR^9R^{10}$, $CO_2R^{11}$, cyano, trifluoromethyl, $NR^9R^{10}$, $NR^9COR^{11}$, $NR^9CONR^9R^{10}$, $NR^9CO_2R^{12}$, $NR^9SO_2R^{13}$, nitro, hydroxy, $C_{1-6}$alkoxy, $OC(O)R^{11}$, $OC(O)NR^9R^{10}$, $SR^{14}$, $SOR^{13}$, $SO_2R^{13}$, $SO_2 NR^9R^{10}$ or halogen. Preferably, X is hydrogen, trifluoromethyl, chloro, or methyl. More preferably, X is trifluoromethyl. When X is trifluoromethyl, X is preferably 3-$CF_3$.

It will be understood that the substituent(s) X may be at any open position on the aromatic ring of formula (I) to which the substituent is attached. In addition, it will be understood that there may be more than one substituent X in any given compound of formula (I), and that if there is more than one substituent X, that substituent may be the same or different.

$R^1$, $R^2$, $R^6$, and $R^7$ are suitably, independently, hydrogen or $C_{1-6}$alkyl. Preferably, $R^1$, $R^2$, $R^6$, and $R^7$ are $C_{1-6}$alkyl. More preferably, $R^1$, $R^2$, $R^6$, and $R^7$ are meth $R^3$ is suitably hydrogen or hydroxy. Preferably $R^3$ is hydrogen.

$R^4$ is suitably hydrogen or $C_{1-6}$alkyl and $R^5$ is suitably hydrogen, $C_{1-6}$alkyl, $C_{3-6}$cycloalkyl, or aralkyl. Preferably, $R^4$ is hydrogen and $R^5$ is $C_{1-6}$alkyl, $C_{3-6}$cycloalkyl, or aralkyl, or $R^4$ and $R^5$ are $C_{1-6}$alkyl. More preferably, $R^4$ is hydrogen and $R^5$ is methyl, cyclopropyl or cyclohexyl, or $R^4$ and $R^5$ are both methyl.

$NR^4R^5$ may suitably formn a heterocyclic ring having 5-, 6-, or 7-members, optionally containing one of oxygen, sulfur or $NR^8$. When $NR^4R^5$ forms a ring, the preferred rings include morpholino and piperazinyl.

A preferred group of compounds of the invention is wherein.

X is hydrogen, trifluoromethyl, chloro or methyl;

$R^1$ and $R^2$ are methyl;

$R^6$ and $R^7$ are methyl;

$R^3$ is hydrogen or hydroxy; and $R^4$ is hydrogen or $C_{1-6}$alkyl, preferably methyl, and $R^5$ is hydrogen, $C_{1-6}$alkyl, $C_{3-6}$cycloalkyl, or aralkyl; or $NR^4R^5$ forms a 5–7 membered ring, optionally containing one of oxygen, sulfur, or $NR^8$.

A more preferred group of compounds of the invention is wherein:

X is trifluoromethyl;

$R^1$ and $R^2$ are methyl;

$R^6$ and $R^7$ are methyl;

$R^3$ is hydrogen or hydroxy; and $R^4$ is hydrogen or methyl and $R^5$ is hydrogen, methyl, cyclopropyl or cyclohexyl, or $R^4$ and $R^5$ are methyl, or $NR^4R^5$ forms a ring which is morpholino or piperazinyl.

Among the preferred compounds of the invention are the following compounds:

3,4,7,8-Tetrahydro-2,2,8,8-tetramethyl-4-morpholino-6-(3-trifluoromethylphenyl)-2H,6H-benzo[1,2-b:5,4-b'] dipyran;

N-Cyclopropyl-3,4,7,8-tetrahydro-2,2,8,8-tetramethyl-6-(3-trifluoromethylphenyl)-2H,6H-benzo[1,2-b:5,4-b'] dipyran4-amine;

N-Cyclohexyl-3,4,7,8-tetrahydro-2,2,8,8-tetramethyl-6-(3-trifluoromethylphenyl)-2H,6H-benzo[1,2-b:5,4-b'] dipyran-4-amine;

3,4,7,8-Tetrahydro-4-(4-methylpiperazin-1-yl)-2,2,8,8-tetramethyl-6-(3-trifluoromethylphenyl)-2H,6H-benzo [1,2-b:5,4-b']dipyran;

N-Benzyl-3,4,7,8-tetrahydro-2,2,8,8-tetramethyl-6-(3-trifluoromethylphenyl)-2H,6H-benzo[1,2-b:5,4-b'] dipyran-4-amine;

3,4,7,8-Tetrahydro-N-methyl-2,2,8,8-tetramethyl-6-(3-trifluoromethylphenyl)-2H,6H-benzol[1,2-b:5,4-b'] dipyran-4-amine hydrochloride;

3,4,7,8-Tetrahydro-N-methyl-2,2,8,8-tetramethyl-6-(3-trifluoromethylphenyl)-2H,6H-benzo[1,2-b:5,4-b'] dipyran-4-amine (isomer 1);

3,4,7,8-Tetrahydro-N-methyl-2,2,8,8-tetramethyl-6-(3-trifluoromethylphenyl)-2H,6H-benzo[1,2-b:5,4-b'dipyran-4-amine (isomer 2)(;

3,4,7,8-Tetrahydro-N-methyl-2,2,8,8-tetramethyl-6-(3-trifluoromethylphenyl)-2H,6H-benzo[1,2-b:5,4-b'] dipyran-4-amine (isomer 3);

3,4,7,8-Tetrahydro-N-methyl-2,2,8,8-tetramethyl-6-(3-trifluoromethylphenyl)-2H,6H-benzo[1,2-b:5,4-b'] dipyran-4-amine (isomer 4);

3,4,7,8-Tetrahydro-N-methyl-2,2,8,8-tetramethyl-6-phenyl-2H,6H-benzo-[1,2-b:5,4-b']dipyran-4-amine hydrochloride;

6-(3-Chlorophenyl)-3,4,7,8-tetrahydro-N-methyl-2,2,8,8-tetramethyl-2H,6H-benzo[1,2-b:5,4-b']dipyran-4-amine;

6-(4-Chlorophenyl)-3,4,7,8-tetrahydro-N-methyl-2,2,8,8-tetramethyl-2H,6H-benzo[1,2-b:5,4-b']dipyran-4-amine hydrochloride;

3,4,7,8-Tetrahydro-N-methyl-6-(4-methylphenyl)-2,2,8,8-tetramethyl-2H,6H-benzo[1,2-b:5,4-b']dipyran-4-amine;

3,4,7,8-Tetrahydro-6-(4-methoxyphenyl)-N-methyl-2,2,8,8-tetramethyl-2H,6H-benzo[1,2-b:5,4-b']dipyran-4-amine;

3,4,7,8-Tetrahydro-N,N-dimethyl-2,2,8,8-tetramethyl-6-(3-trifluoromethylphenyl)-2H,6H-benzo[1,2-b:5,4-b'] dipyran-4-amine hydrochloride, (4α)-3,4,7,8-Tetrahydro-3β-hydroxy-N,N-dimethyl-2,2,8,8-tetramethyl-6β-(3-trifluoromethylphenyl)-2H,6H-benzo[1,2-b:5,4-b']dipyran-4-amine hydrochloride hydrate; and (4β)-3,4,7,8-tetrahydro-3α-hydroxy-N,N-dimethyl-2,2,8,8-tetramethyl-6β-(3-trifluoromethylphenyl)-2H,6H-benzo[1,2-b:5,4-b']dipyran-4-amine hydrochloride.

Compounds excluded from the scope of this invention are as follows:

4-(4-Benzylpiperazin-1-yl)-3,4,7,8-tetrahydro-2,2,8,8-tetramethyl-6-(3-trifluoromethylphenyl)-2H,6H-benzo[1,2-b:5,4-b']dipyran; and N-tert-butyl-3,4,7,8-tetrahydro-2,2,8,8-tetramethyl-6-(3-trifluoromethylphenyl)-2H,6H-benzo-[1,2-b:5,4-b']dipyran-4-amine.

Formulation of Pharmaceutical Compositions

The pharmaceutically effective compounds of this invention (and the pharmaceutically acceptable salts thereof) are administered in conventional dosage forms prepared by combining a compound of formula (I) ("active ingredient") in an amount sufficient to treat asthma and a topic disorders (for example, a topic dermatitis and allergies), rheumatoid arthritis, atherosclerosis, psoriasis, autoimmune diseases such as multiple sclerosis, inflammatory bowel disease, and HIV infection, with standard pharmaceutical carriers or diluents according to conventional procedures well known in the art. These procedures may involve mixing, granulating and compressing or dissolving the ngredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1000 mg. When a liquid carrier is used, the preparation will be in the form of a syrup, emulsion, soft gelatin capsule, sterile injectable liquid such as an ampule or nonaqueous liquid suspension.

The active ingredient may also be administered topically to a mammal in need of treatment or prophylaxis of CCR5 mediated disease states. The amount of active ingredient required for therapeutic effect on topical administration will, of course, vary with the compound chosen, the nature and severity of the disease state being treated and the mammal undergoing treatment, and is ultimately at the discretion of the physician. A suitable dose of an active ingredient is 1.5 mg to 500 mg for topical administration, the most preferred dosage being 1 mg to 100 mg, for example 5 to 25 mg administered two or three times daily.

By topical administration is meant non-systemic administration and includes the application of the active ingredient externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous or alcoholic solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol. The formulation may incorporate any suitable surface active agent such as an anionic, cationic or non-ionic surfactant such as esters or polyoxyethylene derivatives thereof. Suspending agents such as natural gums, cellulose derivatives or inorganic materials such as silicaceous silicas, and other ingredients such as lanolin, may also be included.

The active ingredient may also be administered by inhalation. By "inhalation" is meant intranasal and oral inhalation administration. Appropriate dosage forms for such administration, such as an aerosol formulation or a metered dose inhaler, may be prepared by conventional techniques. The daily dosage amount of the active ingredient administered by inhalation is from about 0.1 mg to about 100 mg per day, preferably about 1 mg to about 10 mg per day.

In one aspect, this invention relates to a method of treating asthma and a topic disorders (for example, a topic dermatitis and allergies), COPD, rheumatoid arthritis, sarcoidosis and other fibrotic diseases, atherosclerosis, psoriasis, autoimmune diseases such as multiple sclerosis, inflammatory bowel disease, and HIV infection, all in mammals, preferably humans, which comprises administering to such mammal an effective amount of a CCR5 receptor modulator, in particular, a compound as depicted in formula (I).

By the term "treating" is meant either prophylactic or therapeutic therapy. Such formula (I) compound can be administered to such mammal in a conventional dosage form prepared by combining the formula (I) compound with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. The formula (I) compound is administered to a mammal in need of treatment for CCR5-mediated diseases in an amount sufficient to decrease symptoms associated with these diseases. The route of administration may be oral or parenteral.

The term parenteral as used herein includes intravenous, intramuscular, subcutaneous, intra-rectal, intravaginal or intraperitoneal administration. The subcutaneous and intramuscular forms of parenteral administration are generally preferred. The daily parenteral dosage regimen will preferably be from about 30 mg to about 300 mg per day of active ingredient. The daily oral dosage regimen will preferably be from about 100 mg to about 2000 mg per day of active ingredient.

It will be recognized by one of skill in the art that the optimal quantity and spacing of individual dosages of a formula (I) compound will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of the formula (I) compound given per day for a defined number of days, can be ascertained by those skilled in the art using conventional course of treatment determination tests.

Methods of Preparation

The compounds of formula (I) can be prepared by art-recognized procedures from known or commercially available starting materials. If the starting materials are unavailable from a commercial source, their synthesis is described herein, or they can be prepared by procedures known in the art.

Specifically, compounds of formula (I) wherein $R^3$ is hydrogen are prepared by methods known to the art. For example, in Scheme 1, resorcinol (1-1) and 3,3-dimethylacrylic acid are treated with a suitable reagent, such as sulfuric acid, polyphosphoric acid or boron trifluoride etherate, at a suitable temperature, such as 25–100° C., for a suitable time, such as overnight, to give chromanone 1-2. The phenolic hydroxyl group in 1-2 is protected by reaction with a suitable alkylating agent, such as benzyl bromide, in the presence of a suitable base, such as potassium carbonate, in a suitable solvent, such as acetone, at a suitable temperature, such as reflux, for a suitable time, such as 22 hours, to give 1-3. 1-3 is reacted with a suitable organometallic reagent, such as with phenyl Grignard or a substituted phenyl Grignard reagent in a suitable solvent, such as ether, at a suitable temperature, such as reflux, for a suitable time, such as 16 hours, to give the substituted chromene 1-4. The double bond in chromene 1-4 is reduced and the protecting benzyl group removed to give substituted chroman 1-5 by treatment with hydrogen and a suitable catalyst, such as palladium-on-carbon, in a suitable solvent, such as ethanol, at a suitable temperature, such as room temperature, for a suitable time, such as 3 hours. Chroman 1-5 is converted to the benzo-dipyranone 1-6 by treatment with 3,3-dimethylacrylic acid and a suitable agent, such as boron trifluoride etherate, sulfuric acid or polyphosphoric acid, at a suitable temperature, such as room temperature, for a suitable time, such as overnight. Benzo-dipyranone 1-6 is converted to benzo-dipyranamine 1-7 by treatment with a suitable amine, such as methylamine, in the presence of a suitable catalyst, such as titanium tetrachloride, in a suitable solvent, such as benzene, at a suitable temperature, such as room temperature, for a suitable time, such as three days, followed by treatment with a suitable reducing agent, such as sodium borohydride, in a suitable solvent, such as methanol, at a suitable temperature, such as room temperature, for a suitable time, such as one hour.

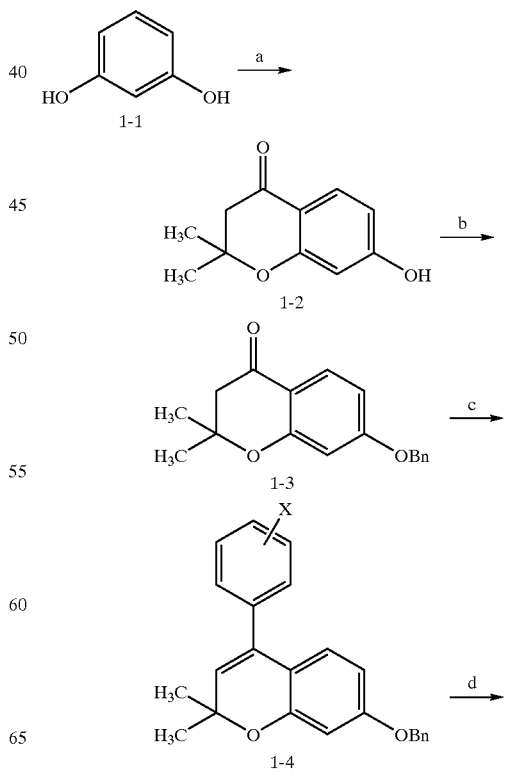

Scheme 1

11
-continued

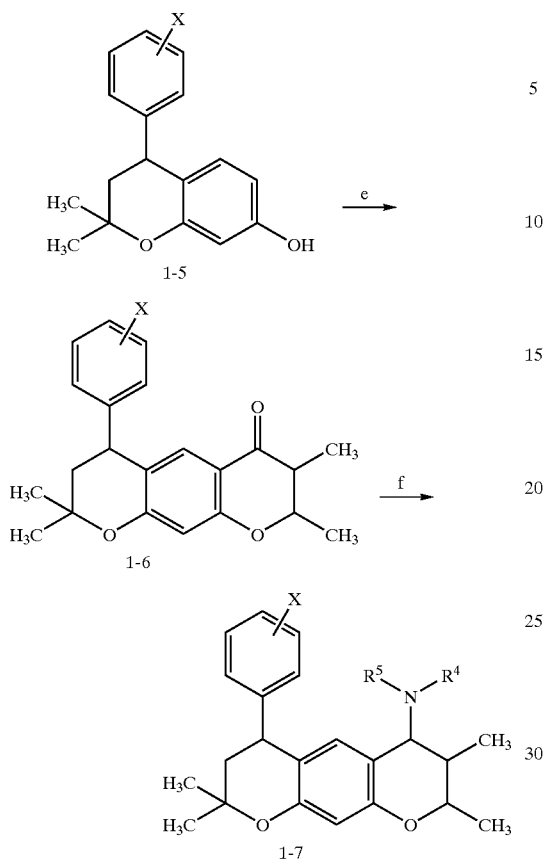

a) 3,3-dimethylacrylic acid; H$_2$SO$_4$; b) benzyl bromide, K$_2$CO$_3$, acetone; c) bromo-X-benzene, Mg, ether: d) H$_2$, 10% Pd/C, EtOH; e) 3,3-dimethylacrylic acid, BF$_3$ etherate; f) HNR$^4$R$^5$, TiCl$_4$, benzene; NaBH$_4$, MeOH Compounds of formula (I) where R$^3$ is hydroxyl are prepared by methods known to the art. For example, in Scheme 2, compound 1-6 is converted to the benzodipyranol 2-1 by reduction of the ketone with a suitable reagent, such as lithium aluminum hydride, in a suitable solvent, such as ether, at a suitable temperature, such as at reflux. Compound 2-1 is dehydrated with a suitable reagent, such as hydrochloric acid, to give the dihydro-benzodipyran 2-2. Compound 2-2 is converted to benzodipyran oxide 2-3 by treatment with a suitable reagent, such as iodine, in a suitable solvent, such as dioxane, followed by treatment with a suitable reagent, such as silver oxide. The epoxide 2-3 is converted to the hydroxy-benzodipyranarnine 24 by treatment with a suitable reagent, such as dimethylamine, in a suitable solvent, such as ethanol, at a suitable temperature, such as room temperature, for a suitable time, such as two days.

12

Scheme 2

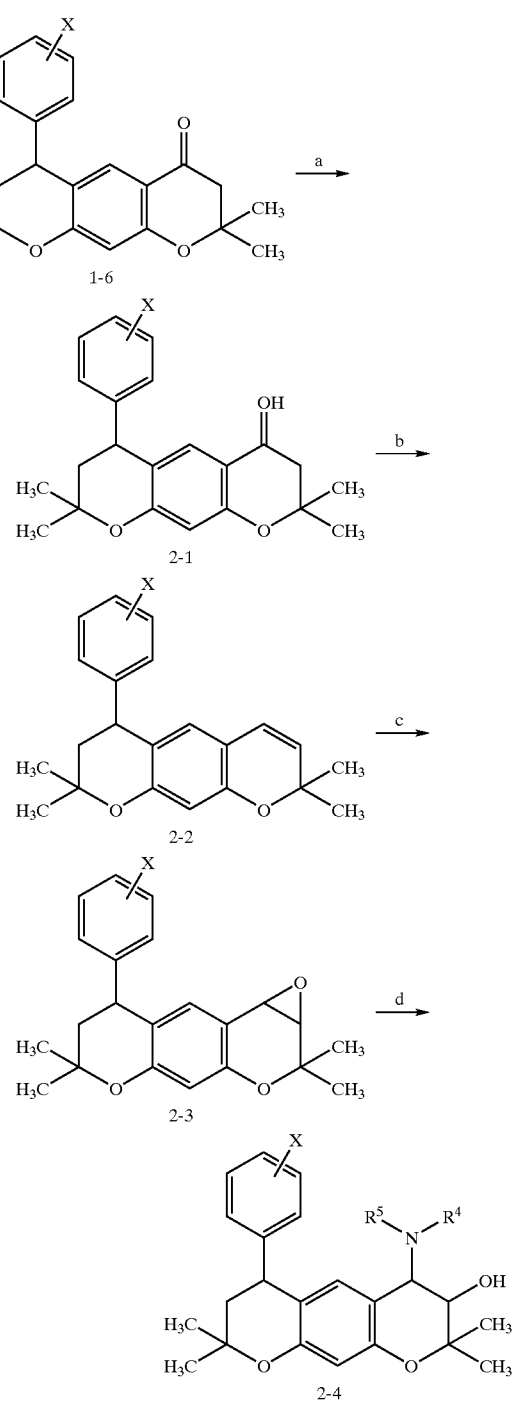

a) LiAlH$_4$, Δ, Et$_2$O; H$_2$O; b) aq HCl; c) I$_2$, dioxane; Ag$_2$O; d) HNR$^4$R$^5$, EtOH Compounds of formula (I) where ═══ is a double bond are prepared by the method of Scheme 1, except substituting 1-5', prepared as described in United States Patent 4,080,335, for 1-5.

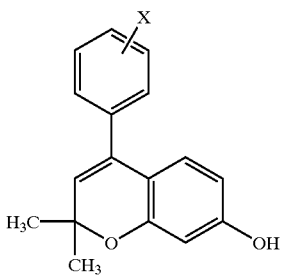

1-5'

Biological Data

CCR5 Receptor Binding Assay

CHO cell membranes (0.25×10⁶ cell equivalents) derived from CHO cells stably transfected with CCR5 were incubated with 0.3 $^{125}$I-RANTES in a 96 well plate for 45 min at room temperature (final reaction volume 200 ul). The reaction was terminated by filtration and the filters (GF/C) were washed twelve times with a solution of phosphate buffered saline containing 0.1 % bovine serum albumin and 0.05% NaN$_3$. The radioactivity bound to filters was measured by liquid scintillation spectrometry. Non-specific binding was determined in the presence of unlabelled RANTES (10 or 30 nM) and averages 30–50% of total binding.

CCR5 Receptor Functional Assay

The cellular functional assay used to assess antagonist activity of compounds was RANTES-induced Ca$^{2+}$ mobilization in RBL 2H3 cells stably expressing the hCCR5 receptor (RBL 2H3 hCCR5). Agonist activity is determined by Ca$^{2+}$ mobilization in the same cells which is inhibitable by a selective CCR5 antagonist. In particular, one or more of isomers 1, 2, 3, and 4 demonstrated agonist activity. Cells were grown to 80–100% confluency in T-150 flasks and washed with phosphate-buffered saline. Cells were lifted from the flasks by treating with 3 mL of 1 mM EDTA for 3 min at room temperature and diluting to 2×10⁶ cells/mL with Krebs Ringer Henseleit buffer (KRH; 118 mM NaCl, 4.6 mM KCl, 25 mM NaHCO$_3$, 1 mM KH$_2$PO$_4$ and 11 mM glucose) containing 5 mM HEPES (pH 7.4), 1 mM CaCl$_2$, 1 mM MgCl$_2$ and 0.1% BSA and centrifuged at 200g for 3 min. Cells were resuspended at 2×10⁶ cells/mL in the same buffer with 2 μM Fura-2AM, and incubated for 35 min at 37° C. Cells were centrifuged at 200×g for 3 min and resuspended in the same buffer without Fura-2AM, then incubated for 15 min at 37° C. to complete the hydrolysis of intracellular Fura-2AM, and then centrifuged as before. Cells (10⁶ cells/mL) were resuspended in cold KRH with 5 mM HEPES (pH 7.4), 1 mM CaCl$_2$, 1 MM MgCl$_2$ and 0.1% gelatin and maintained on ice until assayed. For antagonist studies, aliquots (2 mL) of cells were prewarmed at 37° C. for 5 min in 3 mL plastic cuvettes and fluorescence measured in a fluorometer (Johnson Foundation Biomedical Group, Philadelphia, Pa., USA) with magnetic stirring and temperature maintained at 37° C. Excitation was set at 340 nm and emission set at 510 nm. Various concentrations of antagonists or vehicle were added and fluorescence monitored for ~15 sec to ensure that there was no change in baseline fluorescence, followed by the addition of 33 nM RANTES. Maximal Ca$^{2+}$ attained after 33 nM RANTES stimulation was calculated as described by Grynkiewicz et al., (1985). The percent of maximal RANTES-induced Ca$^{2+}$ was determined for each concentration of antagonist and the IC$_{50}$, defined as the concentration of test compound that inhibits 50% of the maximal 33 nM RANTES response, obtained from the concentration-response curves (5–7 concentrations of antagonists).

The compounds of this invention show CCR5 receptor modulator activity having IC$_{50}$ values in the range of 0.0001 to 100 μM. The full structure/activity relationship has not yet been established for the compounds of this invention. However, given the disclosure herein, one of ordinary skill in the art can utilize the present assays in order to determine which compounds of formula (I) are modulators of the CCR5 receptor and which bind thereto with an IC$_{50}$ value in the range of 0.0001 to 100 μM.

EXAMPLES

Example 1

Preparation of 3,4,7,8-Tetrahydro-N-methyl-2,2,8,8-tetramethyl-6-(3-trifluoromethylphenyl)-2H,6H-benzof1.2-b:5.4-b']dipyran-4-amine Hydrochloride a) 2,3-Dihydro-7-hydroxy-2,2-dimethyl-4H-1-benzopyran-4-one Resorcinol (165 g) and 3,3-dimethylacrylic acid (100 g) were mixed, cooled in an ice bath, and treated carefully with concentrated sulfuric acid (180 mL). The internal temperature rose to 68° C. The mixture turned gradually to a viscous orange mass and the internal temperature dropped to 25° C. The ice bath was removed and stirring was continued overnight at room temperature ("RT") during which the mixture solidified. Small amounts of water and ethyl acetate were carefully added alternatively until the mixture dissolved, and it was transferred to a 5 L conical flask with water (2 L) and ethyl acetate (1.5 L). The organic layer was separated and the aqueous layer was extracted with ethyl acetate. The combined organic layers were washed once with water and carefully treated with solid sodium bicarbonate until effervescence stopped. The organic layer was washed with water, concentrated in vacuo, and the resulting white solid was dissolved in 10% sodium hydroxide. The resulting solution was adjusted to pH 2 with concentrated hydrochloric acid and the resulting solid was filtered, dissolved in boiling glacial acetic acid (220 mL), stirred, diluted with boiling water (220 mL), and immediately cooled. The resulting solid was filtered, washed, and dried in vacuo at 50° C. to give the title compound (120 g).

b) 2,3-Dihydro-2,2-dimethyl-7-(phenylmethoxy)-4H-1-benzopyran-4-one

The compound of Example 1(a) (19.2 g) was dissolved in acetone (300 mL) and benzyl bromide (13.4 mL) was added. The mixture was stirred, treated with anhydrous potassium carbonate (15.1 g), and refluxed for 22 h. The mixture was cooled, filtered, and concentrated in vacuo to yield a brown oil. The residue was refluxed with 60/80 petrol to dissolve excess benzyl bromide and then allowed to sit for 3 d during which crude product solidified. The supernatant was decanted and the solid was dried in vacuo at 55° C. to give the title compound which was used in the next step.

c) 2,2-Dimethyl-7-(phenylmethoxy)-4-(3-trifluoromethylphenyl)-2H-1-benzopyran Magnesium (3.82 g) and several crystals of iodine in dry ether (50 mL) were stirred under nitrogen, and 3-bromobenzotrifluoride (30.92 g) in dry ether (60 mL) was added slowly. After half of the bromobenzotrifluoride was added, the mixture was heated to reflux to start the Grignard formation and the remainder of the bromobenzotrifluoride was added over 0.5 h. The mixture was refluxed for a further 1.5 h and the compound of Example 1(b) (25.84 g) in ether (150 mL) was added over 0.5 h. The mixture was refluxed for 16 h, cooled, and dilute hydrochloric acid was added until the solids dissolved. The organic layer was separated and the aqueous layer was extracted with ether. The combined ether layers were dried (MgSO$_4$) and concentrated in vacuo to give a brown oil which was purified by chromatography (silica gel, 15% ether/petrol) to give the title compound as a pale yellow solid (19.10 g).

d) 3,4-Dihydro-2,2-dimethyl-4-(3-trifluoromethylphenyl)-2H-1-pyran-7-ol

The compound of Example 1(c) (20.12 g) was dissolved in ethanol (250 mL) with heating, 10% palladium-on-carbon (2 g) was added, and the mixture was shaken in a hydrogen atmosphere for 3 h. The mixture was filtered through Hyflo, the solids were washed with acetone, and the combined filtrates were concentrated in vacuo to yield an oil. The oil was dissolved in carbon tetrachloride, diluted with 40/60 petrol, and concentrated in vacuo to afford the title compound as a solid (21.8 g) which was used in the next step without further purification.

e) 3,4,7,8-tetrahydro-2,2,8,8-tetramethyl-4-(3-trifluoromethylphenyl)-2H,6H-benzo[1,2-b:5,4-b']dipyran-6-one The compound of Example 1(d) (18.4 g) and 3,3-dimethylacrylic acid (6.28 g) were stirred together in redistilled boron trifluoride etherate (60 mL) at RT. After stirring overnight, the reaction mixture turned to an orange solid and was allowed to stand for 3 d. The mixture was poured onto ice and extracted several times with ethyl acetate. The mixture was concentrated in vacuo and the resulting orange solid was dissolved in ethanolic hydrogen chloride and refluxed for 3 h. The mixture was concentrated in vacuo to give a fine brown solid which was dissolved in ether and chromatographed (alumina, ether) to give the title compound (18.14 g).

f) 3,4,7,8-Tetrahydro-N-methyl-2,2,8,8-tetramethyl-6-(3-trifluoromethylphenl)-2H,6H-benzo[1,2-b:5,4-b']dipyran-4-amine Hydrochloride The compound of Example 1(e) (1.16 g) was dissolved in dry benzene (10 mL) and treated with several mL of anhydrous methylamine in a flask fitted with a Dry Ice/isopropanol condenser. The mixture was stirred for 5 min, and a solution of titanium(IV) chloride (3.5 mL) was added, followed by dry benzene to give a total volume of 40 mL. The mixture was stirred at RT for 3 d, filtered through Kieselguhr, and the solids washed with ether. The filtrate was concentrated in vacuo to yield a yellow solid which was dissolved in methanol (40 mL). The resulting solution was stirred, treated with sodium borohydride (0.45 g) added slowly, stirred at RT for 1 h, and concentrated inl vacuo. The residue was partitioned between 10% sodium hydroxide and dichloromethane. The organic layer was separated and the aqueous layer extracted twice with dichloromethane. The combined organic layers were dried (MgSO$_4$), filtered, and concentrated in vacuo to yield (0.69 g) of a yellow oily solid which was purified by chromatography (alumina, ether). The hydrochloride salt was obtained from the resulting free base by dissolving in dry ether and adding ethereal hydrogen chloride, filtering, washing with ether, and drying to give the title compound. mp 223–225° C.

Example 2

Preparation of 3,4,7,8-Tetrahydro-N-methyl-2,2,8,8-tetramethyl-6-(3-trifluoromethylphenyl)-2H,6H-benzo[1,2-b:5,4-b']dipyran-4-amine: Isomer 1; and 3,4,7,8-tetrahydro-N-methyl-2,2,8,8-tetramethyl-6-(3-trifluoromethylphenyl)-2H,6H-benzo[1,2-b:5,4-b']dipyran-4-amine: Isomer 2: and 3,4,7,8-tetrahydro-N-methyl-2,2,8,8-tetramethyl-6-(3-trifluoromethylphenyl)-2H,6H-benzo[12-b:5,4-b']dipyran-4-amine: Isomer 3; and 3,4,7,8-tetrabydro-N-methyl-2,2,8,8-tetramethyl-6-(3-trifluoromethylpheny4)-2H,6H-benzo[1.2-b:5.4-b']dipyran-4-amine: Isomer 4

The compound of Example 1(f) was resolved by HPLC (Chiralpak AD, 4.6×250 mm, 1 mL/min., 99:1:0.1:0.1-hexane:ethanol:trifluoroacetic acid:diethylamine, UV detection at 215 nm) to afford isomers 1 and 2:

isomer 1: $t_R$ 12.7 min; MS(ES) m/e 389.3 [M-(CH$_3$NH$_2$)+H]$^+$;

isomer 2: $t_R$ 17.7 min; MS(ES) m/e 389.3 [M-(CH$_3$NH$_2$)+H]$^+$.

and by HPLC (Chiralpak AD, 4.6×250 mm, 1 mL/min, 99:1:0.1-hexane:ethanol:diethylamine, UV detection at 215 nm) to afford isomers 3 and 4:

isomer 3: tR 5.3 min; MS(ES) m/e 389.3 [M-(CH$_3$NH$_2$)+H]$^+$;

isomer 4: tR 7.9 min; MS(ES) m/e 389.3 [M-(CH$_3$NH$_2$)+H]$^+$.

Examples 3–7

Preparation of 3,4,7,8-Tetrahydro-N-methyl-2,2,8,8-tetramethyl-6-phenyl-2H,6H-benzo[1,2-b:5,4-b']dipyran-4-amine Hydrochloride: 6-(3-chlorophenyl)-3,4,7,8-tetrahydro-N-methyl-2,2,8,8-tetramethyl-2H,6H-benzo[1,2-b:5,4-b]'dipyran-4-amine; 6-(4-chlorophenyl)-3,4,7,8-tetrahydro-N-methyl-2,2,8,8-tetramethyl-2H,6H-benzo[1,2-b:5,4-b']dipyran4-amine Hydrochloride: 3,4,7,8-tetrahydro-N-methyl-6-(4-methylphenyl)-2,2,8,8-tetramethyl-2H,6H-benzo[1,2-b:5,4-b']dipyran-4-amine; and 3,4,7.8-tetrahydro-6-(4-methoxyphenyl)-N-methyl-2,2,8,8-tetramethyl-2H,6H-benzo[1,2-b:5,4-b']dipyran-4-amine Following the procedure of Example 1(c)–(f), except substituting bromobenzene, 3-bromochlorobenzene, 4-bromochlorobenzene, 4-bromotoluene, or 4-bromoanisole for 3-bromobenzotrifluoride, the title compounds were prepared:

3,4,7,8-tetrahydro-N-methyl-2,2,8,8-tetramethyl-6-phenyl-2H,6H-benzo-[1,2-b:5,4-b']dipyran-4-amine hydrochloride: MS(ES) mle 352.0 [M+H]$^+$;

6-(3-chlorophenyl)-3,4,7,8-tetrahydro-N-methyl-2,2,8,8-tetramethyl-2H,6H-benzo[1,2-b:5,4-b']dipyran-4-amine: mp (petroleum ether:chloroform) 190–192° C.;

6-(4-chlorophenyl)-3,4,7,8-tetrahydro-N-methyl-2,2,8,8-tetramethyl-2H,6H-benzo[1,2-b:5,4-b']dipyran-4-amine hydrochloride: MS(ES) m/e 386.2 [M+H]$^+$;

3,4,7,8-tetrahydro-N-methyl-6-(4-methylphenyl)-2,2,8,8-tetramethyl-2H,6H-benzo[1,2-b:5,4-b']dipyran-4-amine: MS(ES) m/e 366.2 [M+H]$^+$;

3,4,7,8-tetrahydro-6-(4-methoxyphenyl)-N-methyl-2,2,8,8-tetramethyl-2H,6H-benzo[1,2-b:5,4-b']dipyran-4-amine: MS(ES) m/e 382.2 [M+H]$^+$.

Example 8

Preparation of 3,4,7,8-Tetrahydro-N,N-dimethyl-2,2, 8,8-tetramethyl-6-(3-trifluoromethylphenyl)-2H,6H-benzo[1,2-b:5,4-b']dipyran-4-amine Hydrochloride:

Aqueous formaldehyde (3 mL) was added to a solution of the compound of Example 1(f) (0.52 g) in acetonitrile (30 mL), and the mixture was stirred vigorously and treated with sodium cyanoborohydride (150 mg). After 15 min the pH of the mixture was 11 and acetic acid was added to afford pH5. The resulting mixture was stirred for 16 h at RT, concentrated in vacuo, and the residual red oil was poured into 2N sodium hydroxide, extracted with chloroform (3×75 mL), and the combined organic extract was dried ($Na_2SO_4$) to give the title compound: MS(ES) m/e 434.2 $[M+H]^+$.

Examples 9 and 10

Preparation of (4α)-3,4,7,8-Tetrahydro-3β-hydroxy-N,N-dimethyl-2,2,8,8-tetramethyl-6β-(3-trifluoromethylphenyl)-2H,6H-benzo[1,2-b:5,4-b']dipyran-4-amine Hydrochloride hydrate and (4β)-3,4,7,8-tetrahydro-3α-hydroxy-N,N-dimethy-2,2,8,8-tetramethyl-6β-(3-trifluoromethylphenyl)-2H,6H-benzo[1,2-b:5,4-b']dipyran-4-amine Hydrochloride a) 3,4,7,8-Tetrahydro-2,2,8,8-tetramethyl-6-(3-trifluoromethylphenyl)-2H,6H-benzo[1,2-b:5,4-b']dipyran-4-ol The compound of Example 1(e) (1 g) was dissolved in dry ether (25 mL), stirred, and solid lithium aluminum hydride (0.15 g) was slowly added. The mixture was stirred, heated to reflux for 40 min, and allowed to cool. Water was carefully added dropwise to destroy excess lithium aluminum hydride to give the title compound which was used in the next step without purification.

b) 3,4-dihydro-2,2,8,8-tetramethyl-4-(3-trifluoromethylphenyl)-2H,8H-benzo[1,2-b:5,4-b']dipyran The compound of Example 9(a) in ether was treated with concentrated hydrochloric acid (20 mL), the mixture was vigorously stirred at RT for 20 h, and the layers were separated. The aqueous layer was extracted with ether (50 mL) and the combined organic layers were dried ($MgSO_4$) and concentrated in vacuo to give the title compound as an off-white solid (0.75 g) which was used without further purification in the next reaction.

c) 3,4-Dihydro-2,2,8,8-tetramethyl-4-(3-trifluoromethylphenyl)-2H,8H-benzo[1,2-b:5,4-b']dipyran Oxide The compound of Example 9(b) was dissolved in dioxane (120 mL), stirred, and treated with iodine (4.9 g). Silver oxide (4.49 g) was added followed by water (10 mL), and the mixture was stirred at RT for 24 h. The solution was filtered through Kieselguhr, and the filtrate was concentrated in vacuo to give a yellow oil which was redissolved in ether (300 mL), dried ($MgSO_4$), and filtered. Powdered potassium hydroxide pellets (9.4 g) were added to the filtrate and the mixture was stirred for 3 d, filtered through Kieselguhr, and concentrated in vacuo to give a dark brown solid. The solid was dissolved in ether, washed several times with brine, dried ($MgSO_4$), filtered, and concentrated in vacuo to give the title compound (5.21 g) as a pale yellow solid.

d) (4α)-3,4,7,8-Tetrahydro-3β-hydroxy-N,N-dimethyl-2,2,8,8-tetramethyl-6β-(3-trifluoromethylphenyl)-2H,6H-benzo[1,2-b:5,4-b']dipyran-4-amine Hydrochloride Hydrate and (4β)-3,4,7,8-Tetrahydro-3α-hydroxy-N,N-dimethyl-2,2,8,8-tetramethyl-6p-(3-trifluoromethylphenyl)-2H,6H-benzo[1,2-b:5,4-b']dipyran-4-amine Hydrochloride The compound of Example 9(c) was dissolved in 30% dimethylamine in ethanol (40 mL) and stirred for 2 d. The mixture was concentrated in vacuo and the mixture was taken up in ether to extract remaining dimethylamine. The product was dried in vacuo to yield a mixture of the free bases of the title compounds (5.27 g) which were separated by chromatography (silica gel, 20–30% ether/petroleum ether) to give the free bases of the title compounds (3.79 g and 1.17 g, respectively). The hydrochlorides were obtained by solution in ether and treatment with excess ethanolic hydrogen chloride:

(4α)-3,4,7,8-tetrahydro-3β-hydroxy-N,N-dimethyl-2,2,8,8-tetramethyl-6β-(3-trifluoromethylphenyl)-2H,6H-benzo[1,2-b:5,4-b']dipyran-4-amine Hydrochloride Hydrate: mp (1:1 ethanol:ether) 200–203° C.; and (4β)-3,4,7,8-tetrahydro-3α-hydroxy-N,N-dimethyl-2,2,8,8-tetramethyl-6β-(3-trifluoromethylphenyl)-2H,6H-benzo[1,2-b:5,4-b']dipyran-4-amine hydrochloride: mp (1:1 ethanol:ether) 195–197° C.

Examples 11–15

Preparation of 3,4,7,8-Tetrahydro-2,2,8,8-tetramethyl-4-morpholino-6-(3-trifluoromethylphenyl)-2H,6H-benzo[1,2-b:5,4-b']dipyran; N-cyclopropyl-3,4,7,8-tetrahydro-2,2,8,8-tetramethyl-6-(3-trifluoromethylphenyl)-2H,6H-benzo[1,2-b:5,4-b']dipyran-4-amine: N-cyclohexyl-3,4,7,8-tetrahydro-2,2,8,8-tetramethyl-6-(3-trifluoromethylphenyl)-2H,6H-benzo[1.2-b:5,4-b']dipyran-4-amine; 3,4,7,8-tetrahydro-4-(4-methylpiperazin-1-yl)-2,2,8,8-tetramethyl-6-(3-trifluoromethylphenyl)-2H,6H-benzo[1,2-b:5,4-b']dipyran: and N-benzyl-3,4,7,8-tetrahydro-2,2,8,8-tetramethyl-6-(3-trifluoromethylphenyl)-2H,6H-benzo[1,2-b:5,4-b']dipyran-4-amine Following the procedure of Example 1(f), except substituting morpholine, cyclopropylamine, cyclohexylamine, 1-methylpiperazine, or benzylamine for methylamine, gave the title compounds:

3,4,7,8-tetrahydro-2,2,8,8-tetramethyl-4-morpholino-6-(3-trifluoromethylphenyl)-2H,6H-benzo[1,2-b:5,4-b']dipyran: MS(ES) m/e 476.1 $[M+H]^+$;

N-cyclopropyl-3,4,7,8-tetrahydro-2,2,8,8-tetramethyl-6-(3-trifluoromethylphenyl)-2H,6H-benzo[1,2-b:5,4-b']dipyran-4-amine: MS(ES) m/e 389.1 $[M—NHcPr]^+$;

N-cyclohexyl-3,4,7,8-tetrahydro-2,2,8,8-tetramethyl-6-(3-trifluoromethylphenyl)-2H,6H-benzo[1,2-b:5,4-b']dipyran-4-amine: MS(ES) m/e 488.1 $[M+H]^+$;

3,4,7,8-tetrahydro-4-(4-methylpiperazin-1-yl)-2,2,8,8-tetramethyl-6-(3-trifluoromethylphenyl)-2H,6H-benzo[1,2-b:5,4-b']dipyran: MS(ES) m/e 489.1 $[M+H]^+$; and N-benzyl-3,4,7,8-tetrahydro-2,2,8,8-tetramethyl-6-(3-trifluoromethylphenyl)-2H,6H-benzo[1,2-b:5,4-b']dipyran-4-amine: MS(ES) m/e 496.1 $[M+H]^+$.

All publications, including, but not limited to, patents and patent applications cited in this specification, are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration it is believed that one skilled in the art can, given the preceding description, utilize the present invention to its fullest extent. Therefore any examples are to be construed as merely illustrative and not a limitation on the scope of the present invention in any way. The embodiments of the invention in which an exclusive property or privilege is claimed are defined as follows:

What is claimed is:

1. A method of treating a CCR5-mediated disease state in mammals which comprises administering to the mammal an effective amount of a compound of formula (I) or a pharmaceutically acceptable salt thereof:

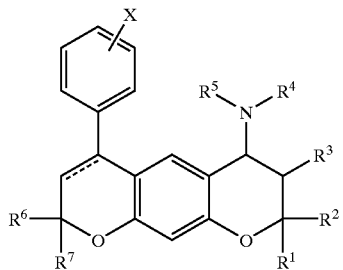

Formula (1)

wherein:

$R^1$, $R^2$, $R^6$, and $R^7$ are independently hydrogen or $C_{1-6}$alkyl;

$R^3$ is hydrogen or hydroxy;

$R^4$ is hydrogen or $C_{1-6}$alkyl;

$R^5$ is hydrogen, $C_{1-6}$alkyl, $C_{3-6}$cycloalkyl, or aralkyl; or, $NR^4R^5$ may form a heterocyclic ring having 5-, 6-, or 7-members, optionally containing one of oxygen, sulfur, or $NR^8$;

$R^8$ is hydrogen, $C_{1-6}$alkyl, or aralkyl;

X is hydrogen or one or more of $C_{1-6}$alkyl, $C_{2-6}$alkenyl, $C_{2-6}$alkynyl, $C_{3-6}$cycloalkyl, $C_{5-6}$cycloalkenyl, aralkyl, aryl, $CH_2NR^9R^{10}$, $CH_2OR^{11}$, $COR^{11}$, $CONR^9R^{10}$, $CO_2R^{11}$, cyano, trifluoromethyl, $NR^9R^{10}$, $NR^9COR^{11}$, $NR^9CONR^9R^{10}$, $NR^9CO_2R^{12}$, $NR^9SO_2R^{13}$, nitro, hydroxy, $C_{1-6}$alkoxy, $OC(O)R^{11}$, $OC(O)NR^9R^{10}$, $SR^{14}$, $SOR^{13}$, $SO_2R^{13}$, $SO_2NR^9R^{10}$ or halogen;

$R^9$ and $R^{10}$ are independently hydrogen, $C_{1-6}$alkyl, aralkyl or aryl; or $NR^9R^{10}$ forms a heterocyclic ring having 5- or 6-members, optionally containing one oxygen, sulfur, or $NR^8$;

$R^{11}$ is hydrogen, $C_{1-6}$alkyl, aralkyl, aryl, or trifluoromethyl;

$R^{12}$ is $C_{1-6}$alkyl, aralkyl, aryl, or trifluoromethyl;

$R^{13}$ is $C_{1-6}$alkyl, aralkyl, aryl, or trifluoromethyl;

$R^{14}$ is hydrogen, $C_{1-6}$alkyl, aralkyl, aryl, or trifluoromethyl; and === is a single or a double bond.

2. The method as claimed in claim 1 wherein the compound of formula (I) is a compound selected from the group consisting of:

3,4,7,8-Tetrahydro-2,2,8,8-tetramethyl-4-morpholino-6-(3-trifluoromethylphenyl)-2H,6H-benzo[1,2-b:5,4-b']dipyran;

N-Cyclopropyl-3,4,7,8-tetrahydro-2,2,8,8-tetramethyl-6-(3-trifluoromethylphenyl)-2H,6H-benzo[1,2-b:5,4-b']dipyran-4-amine;

N-Cyclohexyl-3,4,7,8-tetrahydro-2,2,8,8-tetramethyl-6-(3-trifluoromethylphenyl)-2H,6H-benzo[1,2-b:5,4-b']dipyran-4-amine;

3,4,7,8-Tetrahydro-4-(4-methylpiperazin-1-yl)-2,2,8,8-tetramethyl-6-(3-trifluoromethylphenyl)-2H,6H-benzo[1,2-b:5,4-b']dipyran;

N-Benzyl-3,4,7,8-tetrahydro-2,2,8,8-tetramethyl-6-(3-trifluoromethylphenyl)-2H,6H-benzo[1,2-b:5,4-b']dipyran-4-amine;

3,4,7,8-Tetrahydro-N-methyl-2,2,8,8-tetramethyl-6-(3-trifluoromethylphenyl)-2H,6H-benzo[1,2-b:5,4-b']dipyran-4-amine hydrochloride;

3,4,7,8-Tetrahydro-N-methyl-2,2,8,8-tetramethyl-6-(3-trifluoromethylphenyl)-2H,6H-benzo[1,2-b:5,4-b']dipyran-4-amine (isomer 1);

3,4,7,8-Tetrahydro-N-methyl-2,2,8,8-tetramethyl-6-(3-trifluoromethylphenyl)-2H,6H-benzo[1,2-b:5,4-b']dipyran-4-amine (isomer 2)

3,4,7,8-Tetrahydro-N-methyl-2,2,8,8-tetramethyl-6-(3-trifluoromethylphenyl)-2H,6H-benzo[1,2-b:5,4-b']dipyran4-amine (isomer 3);

3,4,7,8-Tetrahydro-N-methyl-2,2,8,8-tetramethyl-6-(3-trifluoromethylphenyl)-2H,6H-benzo[1,2-b:5,4-b']dipyran-4-amine (isomer 4);

3,4,7,8-Tetrahydro-N-methyl-2,2,8,8-tetramethyl-6-phenyl-2H,6H-benzo-[1,2-b:5,4-b']dipyran-4-amine hydrochloride;

6-(3-Chlorophenyl)-3,4,7,8-tetrahydro-N-methyl-2,2,8,8-tetramethyl-2H,6H-benzo[12,2-b:5,4-b']dipyran-4-amine;

6-(4-Chlorophenyl)-3,4,7,8-tetrahydro-N-methyl-2,2,8,8-tetramethyl-2H,6H-benzo[1,2-b:5,4-b']dipyran-4-amine hydrochloride;

3,4,7,8-Tetrahydro-N-methyl-6-(4-methylphenyl)-2,2,8,8-tetramethyl-2H,6H-benzo[1,2-b:5,4-b']dipyran-4-amine;

3,4,7,8-Tetrahydro-6-(4-methoxyphenyl)-N-methyl-2,2,8,8-tetramethyl-2H,6H-benzo[1,2-b:5,4-b']dipyran-4-amine;

3,4,7,8-Tetrahydro-N,N-dimethyl-2,2,8,8-tetramethyl-6-(3-trifluoromethylphenyl)-2H,6H-benzo[1,2-b:5,4-b']dipyran-4-amine hydrochloride;

(4α)-3,4,7,8-Tetrahydro-3β-hydroxy-N,N-dimethyl-2,2,8,8-tetramethyl-6β-(3-trifluoromethylphenyl)-2H,6H-benzo[1,2-b:5,4-b']dipyran-4-amine hydrochloride hydrate; and (4β)-3,4,7,8-tetrahydro-3α-hydroxy-N,N-dimethyl-2,2,8,8-tetramethyl-6β-(3-trifluoromethylphenyl)-2H,6H-benzo[1,2-b:5,4-b']dipyran-4-amine hydrochloride.

3. The method as claimed in claim 1, wherein the disease is selected from the group consisting of COPD, asthma and a topic disorders, rheumatoid arthritis, sarcoidosis, atherosclerosis, psoriasis, autoinmmune diseases, multiple sclerosis, inflammatory bowel disease, and HIV infection.

4. A compound of formula (I) or a pharmaceutically acceptable salt thereof:

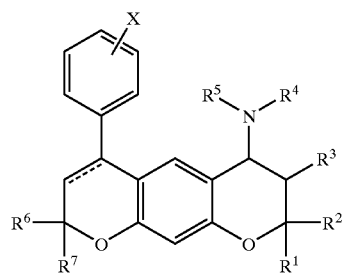

Formula (1)

wherein:

$R^1$, $R^2$, $R^6$, and $R^7$ are independently hydrogen or $C_{1-6}$alkyl;

R³ is hydrogen or hydroxy;

R⁴ is hydrogen or $C_{1-6}$alkyl;

R⁵ is hydrogen, $C_{1-6}$alkyl, $C_{3-6}$cycloalkyl, or aralkyl; or, NR⁴R⁵ may form a heterocyclic ring having 5-, 6-, or 7-members, optionally containing one of oxygen, sulfur, or NR⁸;

R⁸ is hydrogen, $C_{1-6}$alkyl, or aralkyl;

X is hydrogen or one or more of $C_{1-6}$alkyl, $C_{2-6}$alkenyl, $C_{2-6}$alkynyl, $C_{3-6}$cycloalkyl, $C_{5-6}$cycloalkenyl, aralkyl, aryl, $CH_2NR^9R^{10}$, $CH_2OR^{11}$, $COR^{11}$, $CONR^9R^{10}$, $CO_2R^{11}$, cyano, trifluoromethyl, $NR^9R^{10}$, $NR^9COR^{11}$, $NR^9CONR^9R^{10}$, $NR^9CO_2R^{12}$, $NR^9SO_2R^{13}$, nitro, hydroxy, $C_{1-6}$alkoxy, $OC(O)R^{11}$, $OC(O)NR^9R^{10}$, $SR^{14}$, $SOR^{13}$, $SO_2R^{13}$, $SO_2 NR^9R^{10}$ or halogen;

R⁹ and R¹⁰ are independently hydrogen, $C_{1-6}$alkyl, aralkyl or aryl; or NR⁹R¹⁰ forms a heterocyclic ring having 5- or 6-members, optionally containing one oxygen, sulfur, or NR⁸;

R¹¹ is hydrogen, $C_{1-6}$alkyl, aralkyl, aryl, or trifluoromethyl;

R¹² is $C_{1-6}$alkyl, aralkyl, aryl, or trifluoromethyl;

R¹³ is $C_{1-6}$alkyl, aralkyl, aryl, or trifluoromethyl;

R¹⁴ is hydrogen, $C_{1-6}$alkyl, aralkyl, aryl, or trifluoromethyl; and ===== is a single or a double bond.

5. The compound as claimed in claim 4 selected from the group consisting of: 3,4,7,8-Tetrahydro-2,2,8,8-tetramethyl-4-morpholino-6-(3-trifluoromethylphenyl)-2H,6H-benzo[1,2-b:5,4-b']dipyran;

N-Cyclopropyl-3,4,7,8-tetrahydro-2,2,8,8-tetramethyl-6-(3-trifluoromethylphenyl)-2H,6H-benzo[1,2-b:5,4-b dipyran-4-amine;

N-Cyclohexyl-3,4,7,8-tetrahydro-2,2,8,8-tetramethyl-6-(3-trifluoromethylphenyl)-2H,6H-benzo[1,2-b:5,4-b'] dipyran-4-amine;

3,4,7,8-Tetrahydro-4-(4-methylpiperazin-1-yl)-2,2,8,8-tetramethyl-6-(3-trifluoromethylphenyl)-2H,6H-benzo [1,2-b:5,4-b']dipyran;

N-Benzyl-3,4,7,8-tetrahydro-2,2,8,8-tetramethyl-6-(3-trifluoromethylphenyl)-2H,6H-benzo[1,2-b:5,4-b'] dipyran-4-amine;

3,4,7,8-Tetrahydro-N-methyl-2,2,8,8-tetramethyl-6-(3-trifluoromethylphenyl)-2H,6H-benzo[1,2-b:5,4-b'] dipyran-4-amine hydrochloride;

3,4,7,8-Tetrahydro-N-methyl-2,2,8,8-tetramethyl-6-(3-trifluoromethylphenyl)-2H,6H-benzo[1,2-b:5,4-b'] dipyran-4-amine (isomer 1);

3,4,7,8-Tetrahydro-N-methyl-2,2,8,8-tetramethyl-6-(3-trifluoromethylphenyl)-2H,6H-benzo[1,2-b:5,4-b'] dipyran4-amine (isomer 2)

3,4,7,8-Tetrahydro-N-methyl-2,2,8,8-tetramethyl-6-(3-trifluoromethylphenyl)-2H,6H-benzo[1,2-b:5,4-b'] dipyran-4-amine (isomer 3);

3,4,7,8-Tetrahydro-N-methyl-2,2,8,8-tetramethyl-6-(3-trifluoromethylphenyl)-2H,6H-benzo[1 ,2-b:5,4-b'] dipyran-4-amine (isomer 4);

3,4,7,8-Tetrahydro-N-methyl-2,2,8,8-tetramethyl-6-phenyl-2H,6H-benzo-[1,2-b:5,4-b']dipyran-4-amine hydrochloride;

6-(3-Chlorophenyl)-3,4,7,8-tetrahydro-N-methyl-2,2,8,8-tetramethyl-2H,6H-benzo[1,2-b:5,4-b']dipyran-4-amine;

6-(4-Chlorophenyl)-3,4,7,8-tetrahydro-N-methyl-2,2,8,8-tetramethyl-2H,6H-benzo[1,2-b:5,4-b']dipyran-4-amine hydrochloride;

3,4,7,8-Tetrahydro-N-methyl-6-(4-methylphenyl)-2,2,8,8-tetramethyl-2H,6H-benzo[1,2-b:5,4-b']dipyran-4-amine;

3,4,7,8-Tetrahydro-6-(4-methoxyphenyl)-N-methyl-2,2,8,8-tetramethyl-2H,6H-benzo[1,2-b:5,4-b']dipyran-4-amine;

3,4,7,8-Tetrahydro-N,N-dimethyl-2,2,8,8-tetramethyl-6-(3-trifluoromethylphenyl)-2H,6H-benzo[1,2-b:5,4-b'] dipyran-4-amine hydrochloride;

(4α)-3,4,7,8-Tetrahydro-3β-hydroxy-N,N-dimethyl-2,2,8,8-tetramethyl-6β-(3-trifluoromethylphenyl)-2H,6H-benzo[1,2-b:5,4-b']dipyran-4-amine hydrochloride hydrate; and (4β)-3,4,7,8-tetrahydro-3(x-hydroxy-N,N-dimethyl-2,2,8,8-tetramethyl-6ö-(3-trifluoromethylphenyl)-2H,6H-benzo[1,2-b:5,4-b']dipyran-4-amine hydrochloride.

6. A pharmaceutical composition comprising a compound according to claim 4, and a pharmaceutically acceptable carrier.

7. A pharmaceutical composition comprising a compound according to claim 5, and a pharmaceutically acceptable carrier.

8. A process for the preparation of a compound as claimed in claim 4, which process comprises either:

a) converting a compound of formula (II):

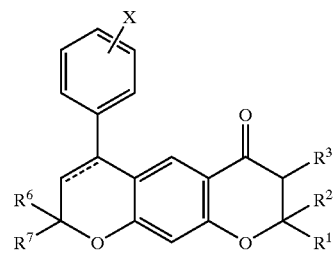

Formula (II)

to a compound of formula (I), wherein R³ is hydrogen and X, R¹, R², R⁶ and R⁷ are defined as in claim 4, by condensation with an amine followed by reduction; or b) (i) reducing the ketone of formula (II) to provide an alcohol of formula (III):

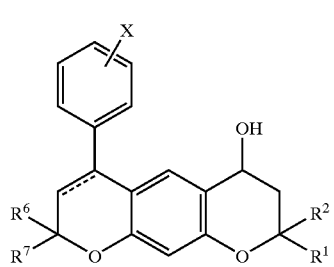

Formula (III)

(ii) converting the compound of formula (III) to an olefin of formula (IV):

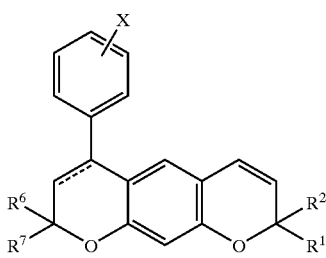

Formula (IV)

(iii) converting the compound of formula (IV) to an epoxide of formula (V):

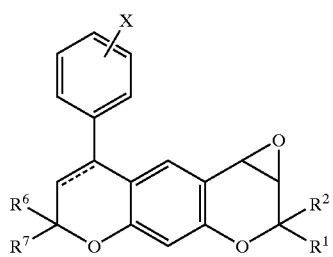

Formula (V)

and (iv) converting the compound of formula (V) by treatment with an amine to the compound of formula (I), wherein $R^3$ is hydroxyl, and X, $R^1$, $R^2$, $R^6$ and $R^7$ are defined as in claim 4.

9. An intermediate compound of formula (II):

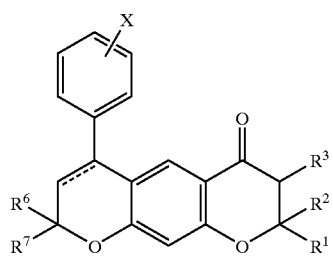

Formula (II)

wherein:

$R^1$, $R^2$, $R^6$, and $R^7$ are independently hydrogen or $C_{1-6}$alkyl;

$R^3$ is hydrogen or hydroxy;

X is hydrogen or one or more of $C_{1-6}$alkyl, $C_{2-6}$alkenyl, $C_{2-6}$alkynyl, $C_{3-6}$cycloalkyl, $C_{5-6}$cycloalkenyl, aralkyl, aryl, $CH_2NR^9R^{10}$, $CH_2OR^{11}$, $COR^{11}$, $CONR^9R^{10}$, $CO_2R^{11}$, cyano, trifluoromethyl, $NR^9R^{10}$, $NR^9COR^{11}$, $NR^9CONR^9R^{10}$, $NR^9CO_2R^{12}$, $NR^9SO_2R^{13}$, nitro, hydroxy, $C_{1-6}$alkoxy, $OC(O)R^{11}$, $OC(O)NR^9R^{10}$, $SR^{14}$, $SOR^{13}$, $SO_2R^{13}$, $SO_2 NR^9R^{10}$ or halogen;

$R^9$ and $R^{10}$ are independently hydrogen, $C_{1-6}$alkyl, aralkyl or aryl; or $NR^9R^{10}$ forms a heterocyclic ring having 5- or 6-members, optionally containing one oxygen, sulfur, or $NR^8$;

$R^{11}$ is hydrogen, $C_{1-6}$alkyl, aralkyl, aryl, or trifluoromethyl;

$R^{12}$ is $C_{1-6}$alkyl, aralkyl, aryl, or trifluoromethyl;

$R^{13}$ is $C_{1-6}$alkyl, aralkyl, aryl, or trifluoromethyl; and $R^{14}$ is hydrogen, $C_{1-6}$alkyl, aralkyl, aryl, or trifluoromethyl.

10. A compound selected from:

3,4,7,8-tetrahydro-2,2,8,8-tetramethyl-4-(3-trifluoromethylphenyl)-2H,6H-benzo[1,2-b:5,4-b'] dipyran-6-one;

3,4,7,8-tetrahydro-2,2,8,8-tetramethyl-6-(3-trifluoromethylphenyl)-2H,6H-benzo[1,2-b:5,4-b'] dipyran-4-ol;

3,4-dihydro-2,2,8,8-tetramethyl-4-(3-trifluoromethylphenyl)-2H,8H-benzo[1,2-b:5,4-b'] dipyran; or 3,4-dihydro-2,2,8,8-tetramethyl-4-(3-trifluoromethylphenyl)-2H,8H-benzo[1,2-b:5,4-b'] dipyran oxide.

* * * * *